(12) United States Patent
Burkhardt et al.

(10) Patent No.: US 7,154,264 B2
(45) Date of Patent: Dec. 26, 2006

(54) SYSTEM AND METHOD USING A COLLAPSABLE COIL FOR INSPECTION OF PIPELINES HAVING INTERNAL RESTRICTIONS

(75) Inventors: Gary L. Burkhardt, Adkins, TX (US); Alfred E. Crouch, San Antonio, TX (US); Jay L. Fisher, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 253 days.

(21) Appl. No.: 10/709,106

(22) Filed: Apr. 14, 2004

(65) Prior Publication Data

US 2004/0217759 A1 Nov. 4, 2004

Related U.S. Application Data

(60) Provisional application No. 60/320,125, filed on Apr. 21, 2003.

(51) Int. Cl.
 *G01N 27/82* (2006.01)
(52) U.S. Cl. .................... 324/220; 324/238
(58) Field of Classification Search ............ 324/219, 324/220, 221, 238, 240
 See application file for complete search history.

(56) References Cited

U.S. PATENT DOCUMENTS 4,769,598 A * 9/1988 Krieg et al. ............ 324/219
5,623,203 A * 4/1997 Hosohara et al. .......... 324/220

OTHER PUBLICATIONS

"Application of Remote-field Eddy Current Testing to Inspection of Unpiggable Pipelines", James Merritt, http://primis.rspa.dot.gov/rd/success.htm listed on document, publication date not available, two pages.*
"Application of Remote-Field Eddy Current (RFEC) Testing to Inspection of Unpiggable Pipelines", Gary L. Burkhardt, Quarterly status and progress report for period ending Mar. 31, 2003, publication date not availble, one page.*

* cited by examiner

*Primary Examiner*—Edward Lefkowitz
*Assistant Examiner*—David M. Schindler
(74) *Attorney, Agent, or Firm*—Taylor Russell & Russell, P.C.

(57) ABSTRACT

The system and method provides a means for inspecting pipelines that have obstructions which prevent conventional inspection pigs from passing the obstructions. The invention uses remote-field eddy current inspection techniques and a uniquely configured excitation coil for inline inspection of pipelines having valves and other fittings that severely restrict or prevent the use of conventional inspection pigs. A unique collapsible excitation coil and a collapsible sensor array enables an inspection pig using these features to pass pipeline obstructions that prevent passage by conventional inspection pigs. The collapsible coil and sensor array provide means for reducing the diameter of an inspection pig to enable it to pass obstructions in the pipeline.

21 Claims, 3 Drawing Sheets

SYSTEM AND METHOD USING A COLLAPSABLE COIL FOR INSPECTION OF PIPELINES HAVING INTERNAL RESTRICTIONS

CROSS REFERENCE TO RELATED APPLICATIONS

This application claims the benefit of U.S. Provisional Application No. 60/320,125, filed on Apr. 21, 2003, which is incorporated herein by reference.

The U.S. Government has a paid-up license in this invention and the right in limited circumstances to require the patent owner to license others on reasonable terms as provided for by the terms of Government Contract No. DTRS 56-02-T-0001 awarded by the U.S. Department of Transportation.

BACKGROUND OF INVENTION

The invention relates generally to nondestructive methods for inspecting steel pipelines for material-loss defects such as corrosion or pits. More particularly, the invention is a system and method that uses remote-field eddy current inspection techniques and a uniquely configured excitation coil for inline inspection of pipelines having valves and other fittings that severely restrict or prevent the use of conventional inspection pigs. The invention relies on a unique collapsible excitation coil and a collapsible sensor array that enables an inspection pig incorporating the invention to pass pipeline obstructions by reducing its diameter to enable it to pass the obstruction.

Pipelines are used extensively in the United States for transporting oil and gas products because of cost, safety and efficiency considerations. Many of these pipelines have been operating for decades. Many long pipelines are buried underground or on an ocean floor, making the cost of repair and maintenance high compared to above ground pipelines. Detection of incipient defects and flaws in these pipelines becomes imperative to prevent environmental damage and costs associated with lost product and pipeline emergency repair.

Detection and characterization of pipeline defects due to material loss, such as corrosion, pits, notches, gouging, etc., are important because of the danger, expense and damage that may result from a loss of integrity of the pipeline due to these defects. Magnetic flux leakage (MFL) is the most widely used inspection technique for in situ pipeline inspection and detection of these defects. MFL inspection pigs use a circumferential array of MFL detectors and strong exciter magnets to magnetize a pipe wall to near magnetic flux saturation density. Material loss in the pipe wall due to defects such as corrosion and pits result in magnetic flux leakage near the pipe wall surface that is detected by the MFL sensors. MFL technology is normally implemented in an inspection pig that travels through a pipeline, propelled by fluid flow.

A limitation of MFL inspection pigs is a result of the structure of the MFL magnet configuration within the inspection pig. The MFL technique requires an array of powerful excitation magnets to magnetize a pipe wall to near saturation of magnetic flux density, most commonly oriented in a direction that is parallel to the longitudinal axis of the pipe. This requires magnets that are large and bulky in order to produce a magnetic field strong enough to approach magnetic flux saturation density. Using this technique, sensors are normally positioned such that they are within this region of a strong magnetic field created by the excitation magnets. Because of the length and bulk required of these magnets, it is difficult to implement a configuration of MFL excitation magnets that is sufficiently collapsible to enable an MFL inspection pig to traverse obstructions such as valves and other fittings within the pipeline. Because of these obstructions, it is not possible to inspect these encumbered pipelines with MFL inspection pigs.

Remote-field eddy current (RFEC) sensing is another established nondestructive testing method that has also been applied to inspection of pipelines. An implementation of this technique is normally located within a pipe, providing a means for detecting defects of pipe wall material on both sides of a pipe wall due to material loss, such as corrosion, pits, notches, gouging, etc. RFEC is a unique form of eddy current testing of pipelines that uses an electromagnetic excitation coil positioned within a pipe such that it is oriented coaxially with the pipeline axis. RFEC excitation coils do not have to produce the magnetic field approaching magnetic flux saturation density as required by MFL magnets. RFEC sensors are located inside the pipe, but are positioned several pipe diameters distance from an excitation coil. This RFEC configuration provides sensors that are in a "remote-field" zone of the magnetic field produced by the coaxial RFEC excitation coil, where direct electromagnetic coupling from the excitation is minimal. The RFEC sensors detect a magnetic field that originated at the excitation coil, penetrated through the pipe wall to the outside diameter, and re-entered the pipe wall to the inside diameter at the sensor location. Since the magnetic field has penetrated the pipe wall, it is strongly affected by the pipe wall thickness, providing detection of defects that result in material loss that changes the pipe wall thickness.

RFEC technology is not routinely applied to pipeline inspection because the MFL method is more straightforward and can have a greater sensitivity. However, for pipelines that have obstructions that prevent MFL inspection pigs from traversing the pipeline, the configuration of an RFEC inspection pig offers an approach that allows an inspection pig to traverse obstructions in the pipeline.

SUMMARY OF INVENTION

The present invention provides a system and method for inspecting pipelines that relies on RFEC technology to enable an inspection pig to traverse obstructions in a pipeline such as valves and other fittings that prevent other inspection pigs from passing. In order to pass internal restrictions in a pipeline, the present invention provides for a collapsible excitation coil and a collapsible sensor array. Although individual sensors in an array may be suspended against a pipe wall to track relatively small variations in pipe diameter to minimize probe liftoff, they require a much greater extent of collapsibility to pass through pipeline restrictions as provided by the present invention. The excitation coil, however, must act electro-magnetically as a single coil with its outer diameter close to the inside diameter if the pipe in order to maintain sensitivity. In the past, the excitation coil has been the limiting factor in allowing an inspection pig to pass through pipeline restrictions.

The RFEC system of the present invention uses a unique excitation coil configuration that can collapse to pass through internal restrictions and then expand to its original diameter when the obstruction is passed. The excitation coil configuration consists of several collapsible segments that are electrically interconnected to produce a magnetic field similar to that produced by a single fixed excitation coil.

An embodiment of the present invention is a remote-field eddy current inspection system for pipe that is capable of collapsing to a smaller diameter to pass through internal restrictions in the pipe and then returning to its original size, that comprises a collapsible excitation coil that functions in a manner similar to a conventional coil when fully deployed and a system of sensors configured on retractable arms. The collapsible excitation coil may comprise segments connected for providing current flow in the periphery of each segment in the same direction as the other segments, and current flows in adjacent legs of each segment that are in opposite directions for canceling the magnetic field produced by current flow in the adjacent legs. The excitation coil segments may be hinged and spring loaded for collapsibility. The excitation coil segments may be connected to arms and rollers for contacting an obstruction and causing the segments to fold before reaching the obstruction. The arms may be arranged so that adjacent segments fold at different times for interleaving to avoid contact with each other.

An embodiment of the claimed invention is a method for inspection of pipelines having internal restrictions, comprising the steps of affixing a collapsible excitation coil to a first end of an inspection pig structure, the inspection pig structure including an instrumentation housing, affixing a collapsible sensor array to a second end opposing the first end of the inspection pig structure, passing the inspection pig structure with the affixed collapsible excitation coil and the affixed collapsible sensor array through a pipeline having internal restrictions, collapsing the excitation coil and the sensor array from an expanded deployed position for enabling the inspection pig structure with the affixed collapsible excitation coil and sensor array to traverse an internal restriction in the pipeline, and returning the affixed collapsible excitation coil and sensor array to an expanded deployed position when the internal restriction has been traversed. The method may further comprise the steps of electrically activating the collapsible excitation coil by excitation circuits in the instrumentation housing, and detecting a remote field eddy current signal by the collapsible sensor array electrically connected to detection circuits in the instrumentation housing for determining defects in a wall of the pipeline. The step of affixing a collapsible excitation coil may further comprise the step of affixing a plurality of electrically interconnected collapsible excitation coil segments. The step of affixing a plurality of electrically interconnected collapsible excitation coil segments may comprise the steps of pivotally hinging each of the plurality of electrically interconnected collapsible excitation coil segments at a center element, the center element being connected to the first end of the inspection pig structure, and spring-loading each excitation coil segment at a center element hinge for maintaining an unobstructed fully expanded deployed position of each excitation coil segment adjacent to an internal wall of the pipeline. The method may further comprise the steps of positioning an arm on each excitation coil segment, the arm having a roller affixed on the arm opposite the excitation coil segment, collapsing and interleaving the excitation coil segments for reducing the diameter of the excitation coil when the rollers encounter internal pipeline restrictions, and returning the collapsed excitation coil segments to fully expanded deployed positions when the rollers do not encounter the internal restrictions. The method may further comprise the step of electrically connecting the excitation coil segments to excitation circuits in the instrumentation housing. The step of affixing a plurality of electrically interconnected collapsible excitation coil segments may further comprise electrically interconnecting the excitation coil segments for flowing a current in an outgoing leg element of a first coil segment in an opposite direction of a current in an adjacent return leg element of a second adjacent coil segment for canceling resultant magnetic fields, and electrically interconnecting the excitation coil segments for flowing a current in a periphery element opposite a center element of each segment in a same circumferential direction. The step of affixing a plurality of electrically interconnected collapsible excitation coil segments may produce a magnetic field substantially equivalent to a magnetic field produced by a non-collapsible excitation coil. The method, wherein maximum diameters of a fully collapsed excitation coil, a fully collapsed sensor array, and the inspection pig structure are less than a minimum internal diameter of the pipeline having internal restrictions for enabling the system to traverse internal restrictions in the pipeline, and maximum diameters of a collapsible excitation coil in a fully expanded deployed position and a collapsible sensor array in a fully expanded deployed position are determined by an internal diameter of the pipeline having internal restrictions. The step of affixing a collapsible sensor array may further comprise the step of affixing a plurality of sensors positioned circumferentially on an internal diameter of the pipeline and electrically connecting the sensors to detection circuits in the instrumentation housing. The step of affixing a plurality of sensors of the sensor array may comprise the steps of pivotally positioning each sensor of the plurality of sensors to a sensor pivot point on a pivot arm, pivotally connecting a structural member pivot point opposite the sensor pivot point on the pivot arm to the second end of the inspection pig structure, spring-loading each pivot arm at the structural member pivot point for maintaining an unobstructed fully expanded deployed position of each pivot arm, collapsing the sensor array sensors for reducing the diameter of the sensor array when the sensors encounter internal pipeline restrictions, and returning the sensor array sensors to expanded deployed positions when the sensors do not encounter the internal restrictions.

Another embodiment of the claimed invention is a system for inspection of pipelines having internal restrictions, comprising means for affixing a collapsible excitation coil comprising a plurality of electrically interconnected collapsible excitation coil segments to a first end of an inspection pig structure, the inspection pig structure including an instrumentation housing, means for affixing a collapsible sensor array to a second end opposing the first end of the inspection pig structure, means for passing the inspection pig structure with the affixed collapsible excitation coil and the affixed collapsible sensor array through a pipeline having internal restrictions, means for collapsing the excitation coil and the sensor array from an expanded deployed position for enabling the inspection pig structure with the affixed collapsible excitation coil and sensor array to traverse an internal restriction in the pipeline, and means for returning the affixed collapsible excitation coil and sensor array to an expanded deployed position when the internal restriction has been traversed. The system may further comprise excitation circuits in the instrumentation housing for electrically activating the collapsible excitation coil, and detection circuits in the instrumentation housing electrically connected to the collapsible sensor array for detecting a remote field eddy current signal by the collapsible sensor array for determining defects in a wall of the pipeline. The means for affixing the plurality of electrically interconnected collapsible excitation coil segments to a first end of an inspection pig structure may comprise hinges for pivotally connecting a center element of each coil segment to the first end of the inspection pig structure, and springs for maintaining an unobstructed fully deployed position of each excitation coil segment adjacent to an internal wall of the pipeline. The system may further comprise an arm positioned on each excitation coil segment having a roller affixed on the arm opposite the excitation coil segment, the excitation coil segments being reduced in diameter by collapsing and interleaving the coil segments when the rollers encounter internal pipeline restrictions, and the excitation coil segments being returned to fully expanded deployed positions when the rollers do not encounter the internal restrictions. The plurality of electrically interconnected collapsible coil segments may be electrically interconnected for flowing a current in a periphery element opposite a center element of each segment in a same circumferential direction, and the plurality of electrically interconnected collapsible coil segments may be electrically interconnected for flowing a current in an outgoing leg element of a first coil segment in an opposite direction of a current in an adjacent return leg element of a second adjacent coil segment for canceling resultant magnetic fields. The plurality of electrically interconnected collapsible coil segments may produce a magnetic field substantially equivalent to a magnetic field produced by a non-collapsible excitation coil. The maximum diameters of a fully collapsed excitation coil, a fully collapsed sensor array, and the inspection pig structure may be less than a minimum internal diameter of the pipeline having internal restrictions for enabling the system to traverse internal restrictions in the pipeline, and the maximum diameters of a collapsible excitation coil in a fully expanded deployed position and a collapsible sensor array in a fully expanded deployed position may be determined by an internal diameter of the pipeline having internal restrictions. The collapsible sensor array may further comprise a plurality of sensors positioned circumferentially on an internal diameter of the pipeline, the sensors being electrically connected to detection circuits in the instrumentation housing. The sensor array may comprise each of the plurality of sensors of the sensor array being pivotally connected to a sensor pivot point on a pivot arm, a structural member pivot point opposite the sensor pivot point on the pivot arm being connected to the second end of the inspection pig structure, each pivot arm being spring-loaded at the structural member pivot point for maintaining an unobstructed fully expanded deployed position of each pivot arm, the sensor array sensors being collapsed for reducing the diameter of the of the sensor array when the sensors encounter internal pipeline restrictions, and the sensor array sensors being returned to expanded deployed positions when the sensors do not encounter the internal restrictions.

Yet another embodiment of the claimed invention is a system for inspection of pipelines having internal restrictions, comprising an inspection pig structure including an instrumentation housing, a collapsible excitation coil including a plurality of electrically interconnected collapsible coil segments affixed to a first end of the inspection pig structure, a collapsible sensor array including a plurality of sensors affixed to a second end of the inspection pig structure opposite the first end, excitation circuits in the instrumentation housing electrically connected to the collapsible excitation coil for exciting the excitation coil to produce a magnetic field outside of a wall of the pipeline, and detector circuits in the instrumentation housing electrically connected to the collapsible sensor array for detecting remote field eddy currents to determine defects in the wall of the pipeline. The maximum diameters of a fully collapsed excitation coil, a fully collapsed sensor array, and the inspection pig structure may be less than a minimum internal diameter of the pipeline having internal restrictions for enabling the system to traverse internal restrictions in the pipeline, and the maximum diameters of a collapsible excitation coil in a fully expanded deployed position and a collapsible sensor array in a fully expanded deployed position are determined by an internal diameter of the pipeline having internal restrictions.

BRIEF DESCRIPTION OF DRAWINGS

These and other features, aspects and advantages of the present invention will become better understood with regard to the following description, appended claims, and accompanying drawings wherein:

DETAILED DESCRIPTION

Figure 1:
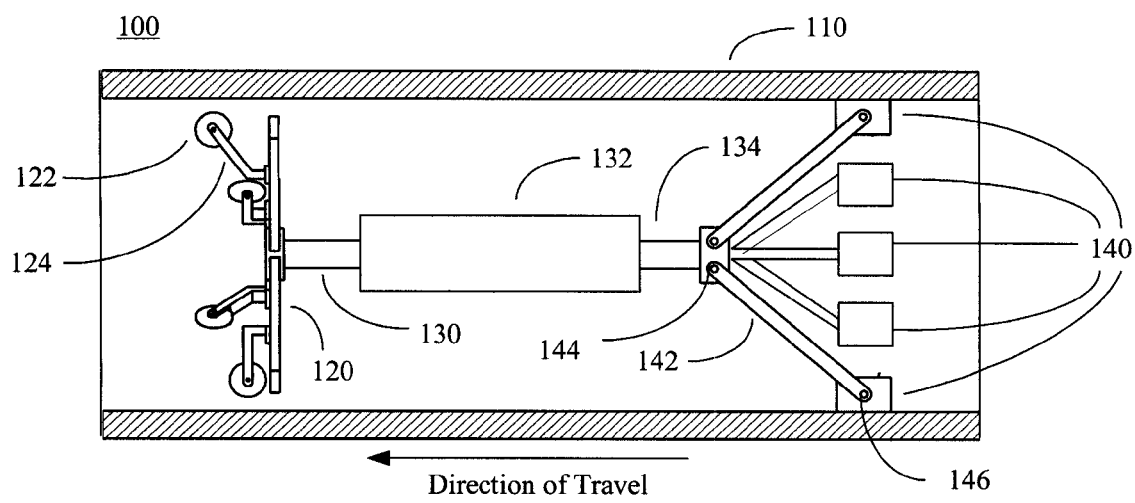
FIG. 1 shows a cut-away section of pipe depicting a RFEC inspection pig according to the present invention.

Turning now to FIG. 1, FIG. 1 shows a cut-away section of pipe 110 depicting a RFEC inspection pig 100 according to the present invention. The RFEC inspection pig 100 comprises a collapsible excitation coil 120 having a plurality of hinged segments, each hinged segment having an attached arm 124 with a roller 122 connected to the arm 124 opposite the segment attachment. The hinged segments are spring-loaded to remain in close proximity to the pipe wall 110. When the rollers 122 contact an obstruction in the pipe 110, the connected arms 124 cause the hinged segments of the excitation coil 120 to collapse to a smaller diameter, enabling the inspection pig 100 to traverse the pipe obstruction. A front member 130 connects the excitation coil 120 to an instrumentation housing 132. Each sensor 140 in a collapsible array of sensors is connected by a pivot arm 142 to a rear member 134, which connects to the instrumentation housing 132. The pivot arms 142 have a sensor pivot point 146 and a structural member pivot point 144 to enable the sensor array 140 to collapse if obstructions are encountered. The pivot arms 142 are spring-loaded to maintain the sensors 140 in the collapsible sensor array in close proximity to the pipe wall 110.

Figure 2:
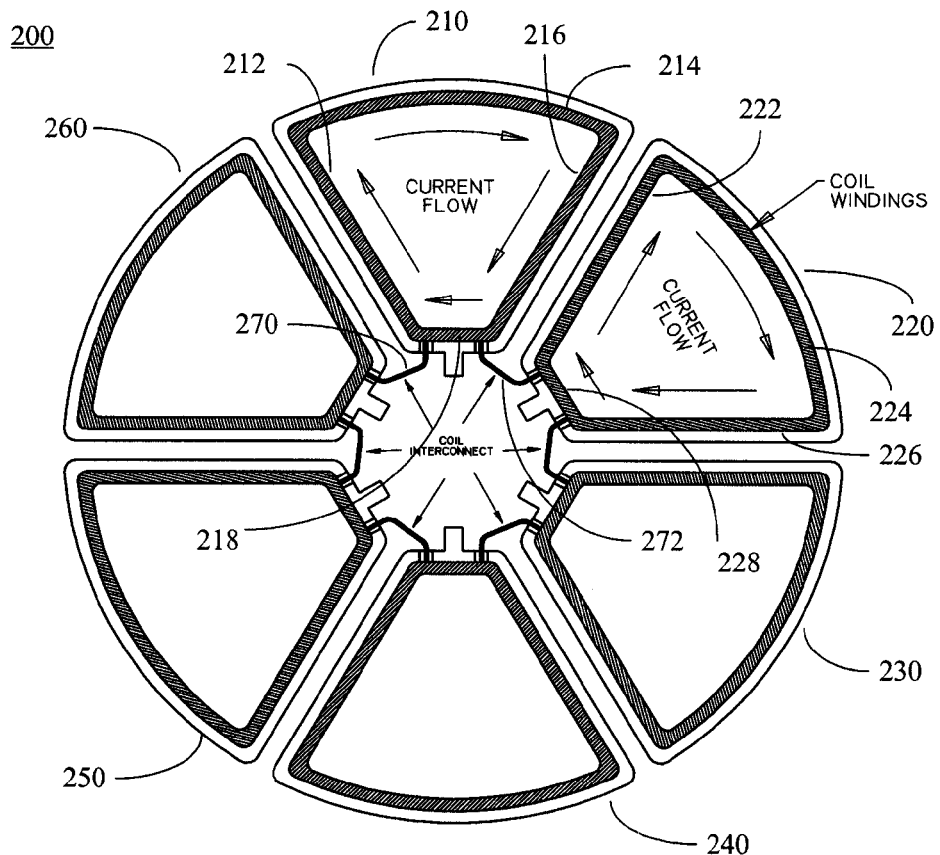
FIG. 2 shows an end view of a collapsible RFEC exciter coil.

Turning to FIG. 2, FIG. 2 shows an end view of a collapsible RFEC exciter coil 200. The collapsible exciter coil 200 comprises a plurality of segments 210, 220, 230, 240, 250, 260 For example, as indicated in FIG. 2, current flow in a first segment 210 flows from an inner leg 218 to the outer periphery through an outgoing leg 212, across a periphery leg 214 and back to the inner leg 218 through a return leg 216. Similarly, current flow in a second segment 220, adjacent to the first segment 210, flows from an inner leg 228 to the outer periphery through an outgoing leg 222, across a periphery leg 224 and back to the inner leg 228 through a return leg 226. Since the current in the outgoing leg 222 is in the opposite direction to the adjacent return leg 216, the magnetic field due to these currents is substantially canceled and does not affect the overall magnetic field produced by the current flowing in the periphery legs. This is the case for each adjacent outgoing and return current legs in each segment 210, 220, 230, 240, 250, 260 of the excitation coil. The current flowing in the inner legs 218, 228 is in the opposite direction from that in the periphery legs 214, 224. Although this inner leg current produces a magnetic field that opposes the main magnetic field produced by current in the periphery legs, it only slightly reduces the main magnetic field because the effective inner diameter is much smaller than the effective outer diameter of the exciter coil. The current flow between the first segment 210 and the second segment 220 is provided by an interconnect link 272. Similarly, each segment is interconnected to an adjacent segment by an interconnect link. In a fully deployed position, the current flow in the outer periphery of each segment is in the same circumferential direction, which is the same as in a single conventional coil. Thus, in the fully deployed position, the segmented excitation coil produces a field similar to that of a conventional coil.

Figure 3:
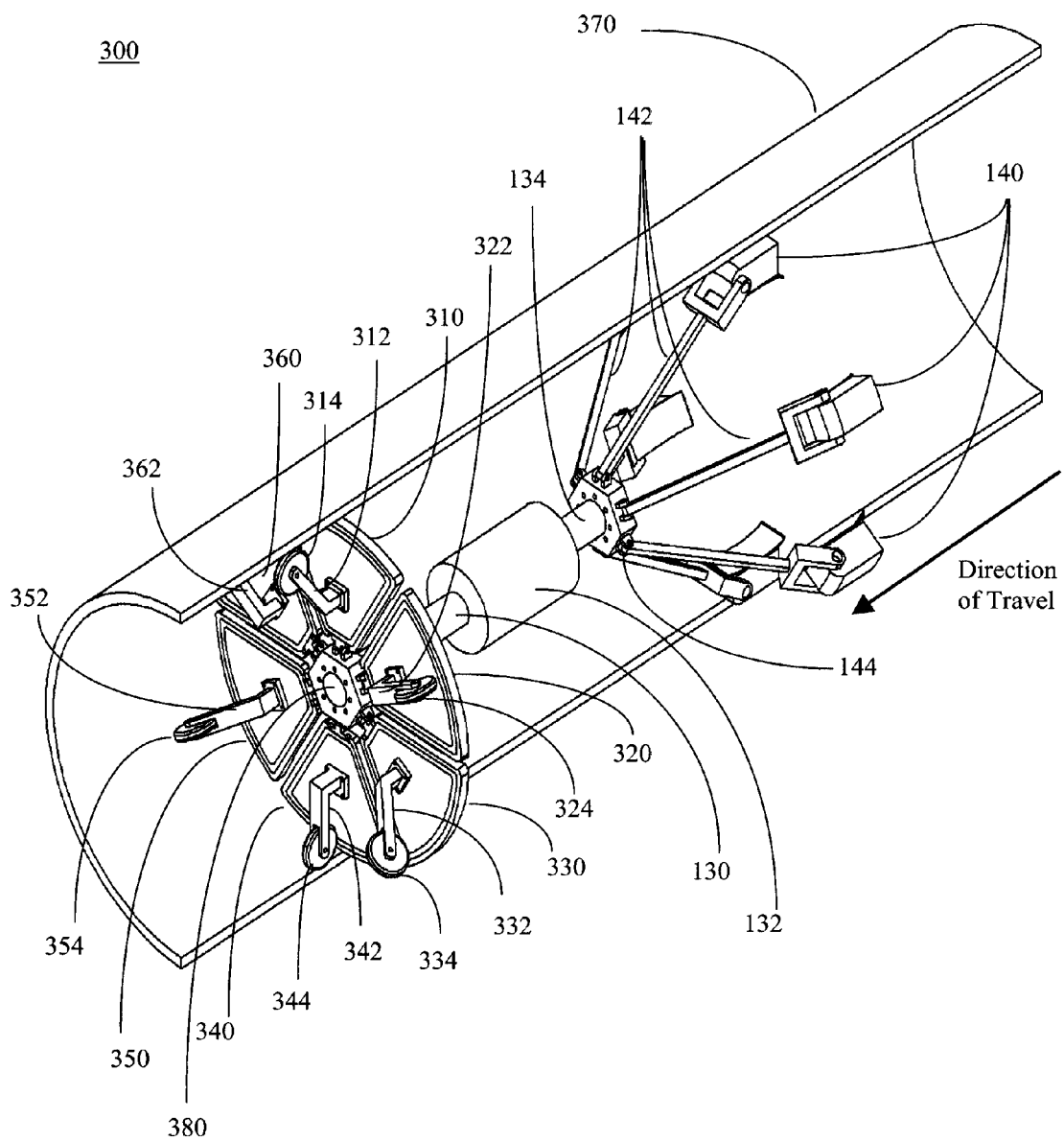
FIG. 3 shows a collapsible excitation coil and sensor array in a fully deployed position.

Turning now to FIG. 3, FIG. 3 shows a collapsible excitation coil and sensor array in a fully deployed position 300. The collapsible excitation coil 310, 320, 330, 340, 350, 360 is positioned within an unrestricted section of pipe 370, as shown in FIG. 3. The excitation coil comprises a plurality of segments 310, 320, 330, 340, 350, 360 that are hinged at a center element 380 and spring-loaded to maintain a fully deployed position until an obstruction in the pipe is encountered. Attached to the front surface of each segment 310, 320, 330, 340, 350, 360 is an arm 312, 322, 332, 342, 352 362 having a roller 314, 324, 334, 344, 354, 364 positioned on the arm opposite the segment surface. Each arm 312, 322, 332, 342, 352, 362 maintains a different angle with respect to a front surface of each segment 310, 320, 330, 340, 350, 360, such that when an obstruction in the pipe 370 is encountered by the segments, each segment 310, 320, 330, 340, 350, 360 collapses for reducing the diameter if the excitation coil 300 to traverse the obstruction. An alternative to maintaining different angles of the arms 312, 322, 332, 342, 352, 362 is to maintain different lengths of the arms 312, 322, 332, 342, 352, 362. When the segments collapse, each segment 310, 320, 330, 340, 350 360 must interleave so that the collapsing operation is staged so that adjacent segments collapse at different times. This is accomplished by the rollers 314, 424, 434, 354, 364 that contact an obstruction and the arms 312, 322, 332, 342, 352, 362 positioned between the rollers 314, 324, 334, 344, 354, 364 and front surface of the segments 310, 320, 330, 340, 350 360 that are positioned at different angles or extend different distances so that some rollers 314, 324, 334, 344, 354, 364 contact the obstruction before others. FIG. 3 also depicts a collapsible array of sensors 140 connected to the collapsible excitation coil 310, 320, 330, 340 350 360, by pivot arm members 142, rear member 134, instrumentation housing 132 and front member 130.

Figure 4:
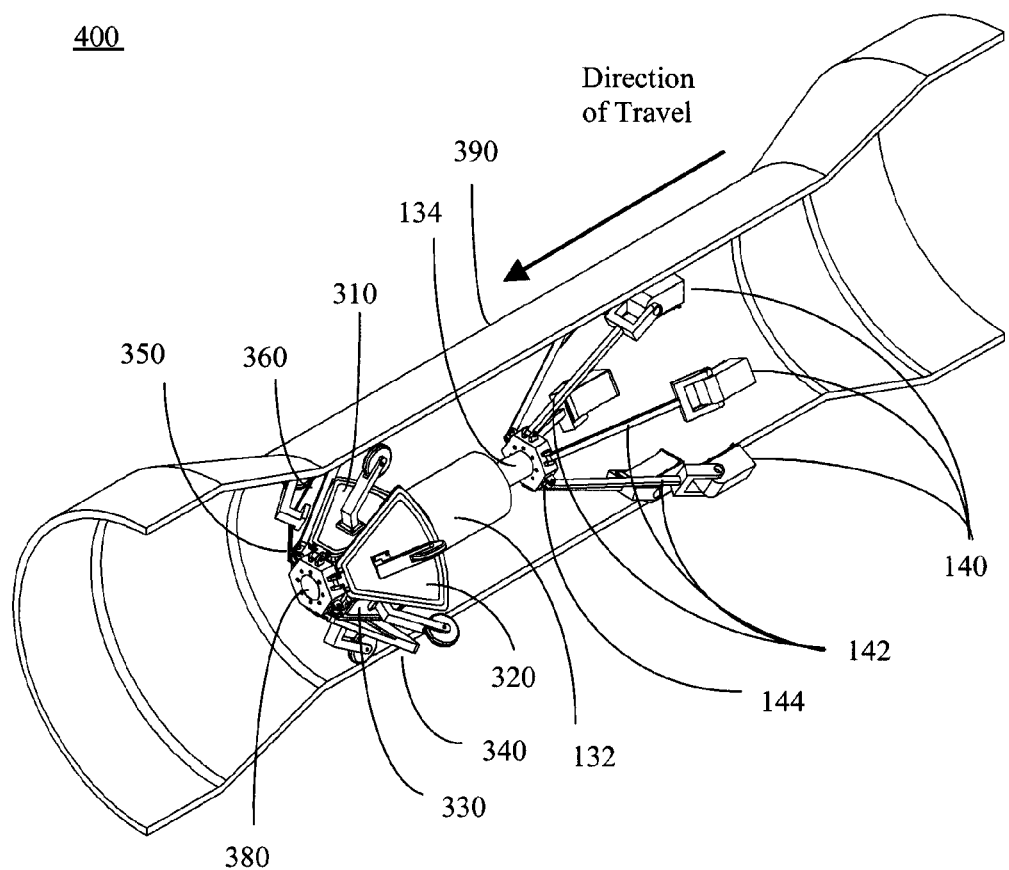
FIG. 4 shows a collapsible excitation coil and sensor array in a partially collapsed position.

Turning now to FIG. 4, FIG. 4 shows a collapsible excitation coil and a sensor array in a partially collapsed position 400. The partially collapsed excitation coil 310, 320, 330, 340, 350 360 is positioned within a restricted section of pipe 390, as shown in FIG. 4, and is a partially collapsed version of the fully deployed excitation coil shown in FIG. 3. The collapsible excitation coil comprises a plurality of segments 310, 320, 330, 340, 350, 360 that are hinged at a center element 380 and spring-loaded to maintain a fully deployed position until an obstruction in the pipe is encountered. When an obstruction is encountered, the segments 310, 320, 330, 340, 350 360 collapse by pivoting on a spring loaded hinged center element 380 to reduce the overall diameter of the excitation coil in order to pass the restricted section of pipe 390. Because of the different angles or different lengths of the arms shown in FIG. 3, the collapsed segments 310, 320, 330, 340, 350, 360 shown in FIG. 4 are interleaved such that adjacent segments do not interfere with one another. FIG. 4 also depicts a collapsible array of sensors wherein each sensor 140 is connected to a pivot arm 142 that pivots on a spring loaded pivot point 144 to reduce the overall diameter of the sensor array. The pivot point 144 is connected to the collapsible excitation coil 310, 320, 330, 340 350 360, by a rear member 134, an instrumentation housing 132 and a front member 130.

Although the present invention has been described in detail with reference to certain preferred embodiments, it should be apparent that modifications and adaptations to those embodiments might occur to persons skilled in the art without departing from the spirit and scope of the present invention.

The invention claimed is:

1. A method for inspection of a pipeline having internal restrictions, comprising the steps of:
    affixing a collapsible excitation coil comprising a plurality of electrically interconnected collapsible excitation coil segments to a first end of an inspection pig structure, the inspection pig structure including an instrumentation housing;
    affixing a collapsible sensor array to a second end opposing the first end of the inspection pig structure;
    passing the inspection pig structure with the affixed collapsible excitation coil and the affixed collapsible sensor array through the pipeline having internal restrictions;
    collapsing the excitation coil and the sensor array from an expanded deployed position for enabling the inspection pig structure with the affixed collapsible excitation coil and sensor array to traverse a first internal restriction in the pipeline; and
    returning the affixed collapsible excitation coil and sensor array to an expanded deployed position when the first internal restriction has been traversed.

2. The method of claim 1, further comprising the steps of:
    electrically activating the collapsible excitation coil by excitation circuits in the instrumentation housing; and
    detecting a remote field eddy current signal by the collapsible sensor array electrically connected to detection circuits in the instrumentation housing for determining defects in a wall of the pipeline.

3. The method of claim 1, wherein the step of affixing a plurality of electrically interconnected collapsible excitation coil segments comprises the steps of:
    pivotally hinging each of the plurality of electrically interconnected collapsible excitation coil segments at a center element, the center element being connected to the first end of the inspection pig structure; and
    spring-loading each excitation coil segment at a center element hinge for maintaining an unobstructed fully expanded deployed position of each excitation coil segment adjacent to an internal wall of the pipeline.

4. The method of claim 3, further comprising the steps of:
    positioning an arm on each excitation coil segment, each arm on each excitation coil segment having a roller affixed on each arm opposite each excitation coil segment;
    collapsing and interleaving each excitation coil segment for reducing a diameter of the excitation coil when a first roller affixed on a first arm encounters a first internal pipeline restriction; and returning each collapsed excitation coil segment to a fully expanded deployed position when the first roller does not encounter the first internal pipeline restriction.

5. The method of claim 1, further comprising the step of electrically connecting the excitation coil segments to excitation circuits in the instrumentation housing.

6. The method of claim 1, wherein the step of affixing a plurality of electrically interconnected collapsible excitation coil segments further comprises:
   electrically interconnecting the excitation coil segments for flowing a current in an outgoing leg element of a first coil segment in an opposite direction of a current in an adjacent return leg element of a second adjacent coil segment for canceling resultant magnetic fields; and
   electrically interconnecting the excitation coil segments for flowing a current in a periphery element opposite a center element of each segment in a same circumferential direction.

7. The method of claim 1, wherein the step of affixing a plurality of electrically interconnected collapsible excitation coil segments produces a magnetic field substantially equivalent to a magnetic field produced by a non-collapsible excitation coil.

8. The method of claim 1, wherein:
   maximum diameters of a fully collapsed excitation coil, a fully collapsed sensor array, and the inspection pig structure are less than a minimum internal diameter of the pipeline having internal restrictions for enabling the system to traverse internal restrictions in the pipeline; and
   maximum diameters of a collapsible excitation coil in a fully expanded deployed position and a collapsible sensor array in a fully expanded deployed position are determined by an internal diameter of the pipeline having internal restrictions.

9. The method of claim 1, wherein the step of affixing a collapsible sensor array further comprises the step of affixing a plurality of sensors positioned circumferentially on an internal diameter of the pipeline and electrically connecting the sensors to detection circuits in the instrumentation housing.

10. The method of claim 9, wherein the step of affixing a plurality of sensors of the sensor array comprises the steps of:
   pivotally positioning each sensor of the plurality of sensors to a sensor pivot point on a pivot arm;
   pivotally connecting a structural member pivot point opposite the sensor pivot point on the pivot arm to the second end of the inspection pig structure;
   spring-loading the pivot arm at the structural member pivot point for maintaining an unobstructed fully expanded deployed position of the pivot arm;
   collapsing the sensor array sensors for reducing a diameter of the of the sensor array when the sensors encounter internal pipeline restrictions; and
   returning the sensor array sensors to expanded deployed positions when the sensors do not encounter the internal pipeline restrictions.

11. A system for inspection of a pipeline having internal restrictions, comprising:
   means for affixing a collapsible excitation coil comprising a plurality of electrically interconnected collapsible excitation coil segments to a first end of an inspection pig structure, the inspection pig structure including an instrumentation housing;
   means for affixing a collapsible sensor array to a second end opposing the first end of the inspection pig structure;
   means for passing the inspection pig structure with the affixed collapsible excitation coil and the affixed collapsible sensor array through the pipeline having internal restrictions; means for collapsing the excitation coil and the sensor array from an expanded deployed position for enabling the inspection pig structure with the affixed collapsible excitation coil and sensor array to traverse a first internal restriction in the pipeline; and
   means for returning the affixed collapsible excitation coil and sensor array to an expanded deployed position when the first internal restriction has been traversed.

12. The system of claim 11, further comprising:
   excitation circuits in the instrumentation housing for electrically activating the collapsible excitation coil; and
   detection circuits in the instrumentation housing electrically connected to the collapsible sensor array for detecting a remote field eddy current signal by the collapsible sensor array for determining defects in a wall of the pipeline.

13. The system of claim 11, wherein the means for affixing the plurality of electrically interconnected collapsible excitation coil segments to a first end of an inspection pig structure comprises:
   hinges for pivotally connecting a center element of each coil segment to the first end of the inspection pig structure; and
   springs for maintaining an unobstructed fully deployed position of each excitation coil segment adjacent to an internal wall of the pipeline.

14. The system of claim 13, further comprising;
   an arm positioned on each excitation coil segment, each arm on each excitation coil segment having a roller affixed on each arm opposite each excitation coil segment;
   each excitation coil segment being reduced in diameter by collapsing and interleaving each coil segment when a first roller affixed on a first arm encounters a first internal pipeline restriction; and each excitation coil segment being returned to a fully expanded deployed position when the first roller does not encounter the first internal pipeline restriction.

15. The system of claim 11, wherein:
   the plurality of electrically interconnected collapsible coil segments are electrically interconnected for flowing a current in a periphery element opposite a center element of each segment in a same circumferential direction; and
   the plurality of electrically interconnected collapsible coil segments are electrically interconnected for flowing a current in an outgoing leg element of a first coil segment in an opposite direction of a current in an adjacent return leg element of a second adjacent coil segment for canceling resultant magnetic fields.

16. The system of claim 11, wherein the plurality of electrically interconnected collapsible coil segments produce a magnetic field substantially equivalent to a magnetic field produced by a non-collapsible excitation coil.

17. The system of claim 11, wherein:
   maximum diameters of a fully collapsed excitation coil, a fully collapsed sensor array, and the inspection pig structure are less than a minimum internal diameter of the pipeline having internal restrictions for enabling the system to traverse internal restrictions in the pipeline; and maximum diameters of a collapsible excitation coil in a fully expanded deployed position and a collapsible sensor array in a fully expanded deployed position are determined by an internal diameter of the pipeline having internal restrictions.

18. The system of claim 11, wherein the collapsible sensor array further comprises a plurality of sensors positioned circumferentially on an internal diameter of the pipeline, the sensors being electrically connected to detection circuits in the instrumentation housing.

19. The method of claim 18, wherein the sensor array comprises:
   each of the plurality of sensors of the sensor array being pivotally connected to a sensor pivot point on a pivot arm;
   a structural member pivot point opposite the sensor pivot point on the pivot arm being connected to the second end of the inspection pig structure;
   the pivot arm being spring-loaded at the structural member pivot point for maintaining an unobstructed fully expanded deployed position of the pivot arm;
   the sensor array sensors being collapsed for reducing the diameter of the of the sensor array when the sensors encounter internal pipeline restrictions; and
   the sensor array sensors being returned to expanded deployed positions when the sensors do not encounter the internal pipeline restrictions.

20. A system for inspection of a pipeline having internal restrictions, comprising:

an inspection pig structure including an instrumentation housing;

a collapsible excitation coil including a plurality of electrically interconnected collapsible coil segments affixed to a first end of the inspection pig structure;

a collapsible sensor array including a plurality of sensors affixed to a second end of the inspection pig structure opposite the first end;

excitation circuits in the instrumentation housing electrically connected to the collapsible excitation coil for exciting the excitation coil to produce a magnetic field outside of a wall of the pipeline; and detector circuits in the instrumentation housing electrically connected to the collapsible sensor array for detecting remote field eddy currents to determine defects in the wall of the pipeline.

21. The system of claim 20, wherein:

maximum diameters of a fully collapsed excitation coil, a fully collapsed sensor array, and the inspection pig structure are less than a minimum internal diameter of the pipeline having internal restrictions for enabling the system to traverse internal restrictions in the pipeline; and maximum diameters of a collapsible excitation coil in a fully expanded deployed position and a collapsible sensor array in a fully expanded deployed position are determined by an internal diameter of the pipeline having internal restrictions.

* * * * *